United States Patent [19]

Jautelat et al.

[11] Patent Number: 5,143,932
[45] Date of Patent: Sep. 1, 1992

[54] MICROBICIDAL HALOGENOALLYL-AZOLYL DERIVATIVES

[75] Inventors: Manfred Jautelat, Burscheid; Klaus Stroech, Solingen; Gerd Hänssler, Leverkusen; Stefan Dutzmann, Hilden; Karl-Heinz Kuck, Langenfeld; Wilhelm Brandes, Leichlingen, all of Fed. Rep. of Germany

[73] Assignee: Bayer Aktiengesellschaft, Leverkusen, Fed. Rep. of Germany

[21] Appl. No.: 645,951

[22] Filed: Jan. 25, 1991

[30] Foreign Application Priority Data

Feb. 3, 1990 [DE] Fed. Rep. of Germany ....... 4003180

[51] Int. Cl.$^5$ ................. A01N 43/653; C07D 249/08
[52] U.S. Cl. ..................................... 514/383; 514/184; 548/101; 548/267.8; 548/268.6
[58] Field of Search ................ 548/101, 267.8, 268.6; 514/184, 383

[56] References Cited

U.S. PATENT DOCUMENTS

| | | | |
|---|---|---|---|
| 4,655,820 | 4/1987 | Worthington et al. | 71/92 |
| 4,871,389 | 10/1989 | Elliott et al. | 71/92 |
| 4,927,833 | 5/1990 | Kirby et al. | 514/399 |

*Primary Examiner*—Patricia L. Morris
*Attorney, Agent, or Firm*—Sprung, Horn, Kramer & Woods

[57] ABSTRACT

Microbicidal halogenoallyl-azolyl derivatives of the formula

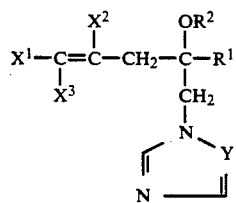

(I)

in which
R$^1$ represents a radical of the formula

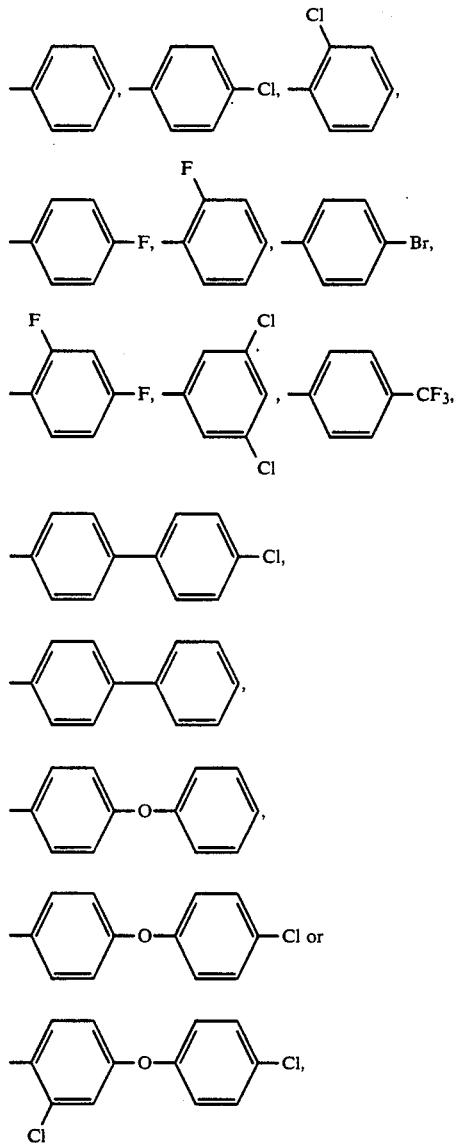

R$^2$ represents hydrogen, alkyl, alkenyl, acyl or aralkyl,
X$^1$ represents halogen,
X$^2$ represents halogen,
X$^3$ represents hydrogen or halogen and
Y represents nitrogen or a CH group, and addition products thereof with acids and metal salts.

9 Claims, No Drawings

MICROBICIDAL HALOGENOALLYL-AZOLYL DERIVATIVES

The present invention relates to new halogenoallyl-azolyl derivatives, to a plurality of processes for their preparation, and to their use as microbicides in plant protection and in the protection of materials.

It has been disclosed that certain dihalogeno-allyl-triazolyl derivatives have fungicidal properties (cf. EP-OS (European Published Specification) 0,097,425). For example, 4-(2,4-dichloro-phenyl)-1,2-dibromo-4-hydroxy-5-(1,2,4-triazol-1-yl)-pent-1-ene and 4-(2,4-dichloro-phenyl)-1,2-dichloro-4-hydroxy-5-(1,2,4-triazol1-yl)-pent-1-ene can be employed for combating fungi. The action of these substances is good, but occasionally leaves something to be desired when applied at low rates.

New halogenoallyl-azolyl derivatives have now been found, of the formula $$X^1-C(X^3)=C(X^2)-CH_2-C(OR^2)(R^1)-CH_2-N(\text{triazolyl/imidazolyl})$$ (I)

in which

R$^1$ represents the radicals of the formulae

[phenyl, 4-chlorophenyl, 2-chlorophenyl, 4-fluorophenyl, 3-fluorophenyl, 4-bromophenyl, 3,4-difluorophenyl, 2,4-dichlorophenyl, 4-trifluoromethylphenyl, 4'-chlorobiphenyl, biphenyl, 4-phenoxyphenyl,]

-continued

[4-(4-chlorophenoxy)phenyl, or 4-(3-chloro-4-chlorophenoxy)phenyl,]

R$^2$ represents hydrogen, alkyl, alkenyl, acyl or aralkyl,
X$^1$ represents halogen,
X$^2$ represents halogen,
X$^3$ represents hydrogen or halogen and
Y represents nitrogen or a CH group, as well as their acid addition salts and metal salt complexes.

The compounds of the formula (I) contain an asymmetrically substituted carbon atom and can therefore be obtained in the two optical isomer forms. Moreover, the substances of the formula (I) can be present in two geometric isomer forms, depending on the position of the halogen atoms on the double bond. The present invention relates to the isomer mixture as well as to the individual isomers.

Furthermore, it has been found that halogenoallyl-azolyl derivatives of the formula (I) as well as the acid addition salts and metal salt complexes thereof are obtained when a) alkynes of the formula $$HC\equiv C-CH_2-C(OR^2)(R^1)-CH_2-N(\text{azolyl})$$ (II)

in which

R$^1$, R$^2$ and Y have the abovementioned meanings, are reacted with halogen or halogen-donating compounds, in the presence of a diluent, or b) alkenes of the formula $$X^1-CH=C(X^2)-CH_2-C(OR^2)(R^1)-CH_2-Z$$ (III)

in which

R$^1$, R$^2$, X$^1$ and X$^2$ have the abovementioned meanings and Z represents halogen, alkylsulphonate or arylsulphonate, are reacted with azoles of the formula $$H-N(\text{azolyl with Y})$$ (IV)

in which
has the abovementioned meaning, in the presence of an acid-binding agent and in the presence of a diluent, or c) alkynes of the formula

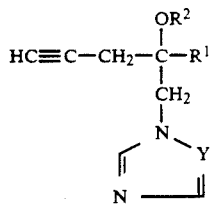

in which
R¹, R² and Y have the abovementioned meanings, are reacted, in a first step, with hypohalites of the formula

    (V)

in which
M represents an alkali metal and
X⁴ represents halogen, in the presence of a diluent, and, in a second step, the resulting halogenoalkynes of the formula

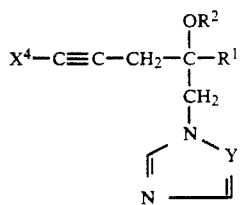

in which
R¹, R², X⁴ and Y have the abovementioned meanings, are reacted with halogen or halogen-donating compounds, in the presence of a diluent, and, if desired, an acid or a metal salt is subsequently added onto the resulting compounds of the formula (I).

Finally, it has been found that the new halogenoallyl-azolyl derivatives of the formula (I) as well as their acid addition salts and metal salt complexes have powerful microbicidal properties and can be employed in plant protection as well as in the protection of materials.

Surprisingly, the substances according to the invention have a better microbicidal activity than the previously known compounds which have the most similar constitution and the same direction of action, both in plant protection and in the protection of materials.

Formula (I) provides a general definition of the halogenoallyl-azolyl derivatives according to the invention. Preferred compounds of the formula (I) are those in which R¹ represents the radicals of the formulae

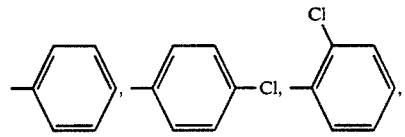

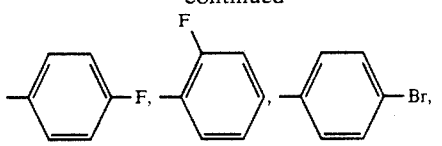

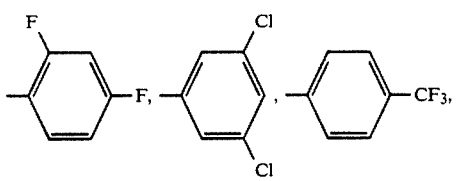

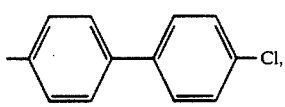

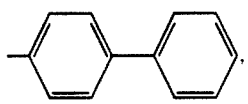

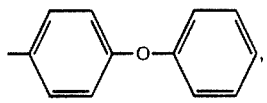

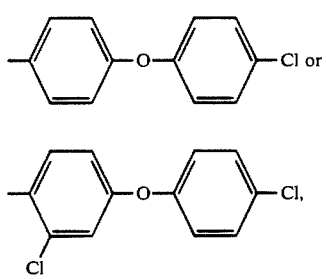

R² represents hydrogen, alkyl having 1 to 6 carbon atoms, alkenyl having 3 to 6 carbon atoms, acyl having 1 to 4 carbon atoms, or phenylalkyl having 1 to 4 carbon atoms in the alkyl moiety, X¹ represents fluorine, chlorine, bromine or iodine,
X² represents fluorine, chlorine, bromine or iodine,
X³ represents hydrogen, chlorine, bromine or iodine, and
Y represents a nitrogen atom or a CH group. Particularly preferred compounds of the formula (I) are those in which R¹ represents the radicals of the formulae

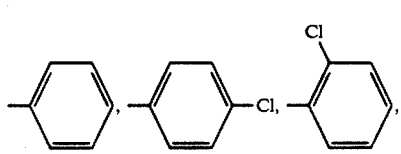

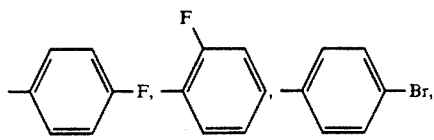

-continued

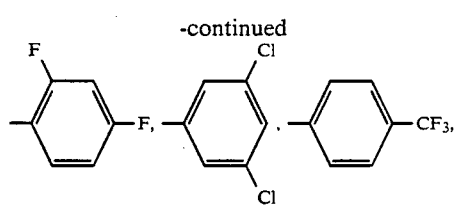

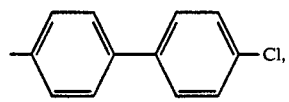

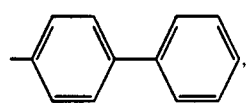

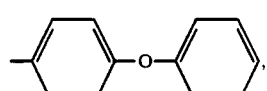

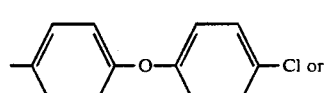

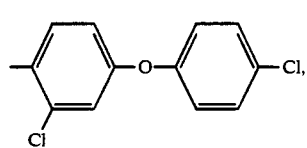

$R^2$ represents hydrogen, methyl, ethyl, n-propyl, isopropyl, n-butyl, allyl, formyl, acetyl, benzyl or phenethyl, $X^1$ represents fluorine, chlorine, bromine or iodine, $X^2$ represents fluorine, chlorine, bromine or iodine, $X^3$ represents hydrogen, chlorine, bromine or iodine, and Y represents a nitrogen atom or a CH group.

Other preferred compounds according to the invention are addition products of acids and those halogenoallyl-azolyl derivatives of the formula (I) in which $R^1$, $R^2$, $X^1$, $X^2$, $X^3$ and Y have those meanings which have been mentioned as being preferred for these substituents.

The acids which can be added on preferably include hydrohalic acids such as, for example, hydrochloric acid and hydrobromic acid, in particular hydrochloric acid, furthermore phosphoric acid, nitric acid, mono- and bifunctional carboxylic acids and hydroxycarboxylic acids such as, for example, acetic acid, maleic acid, succinic acid, fumaric acid, tartaric acid, citric acid, salicylic acid, sorbic acid and lactic acid, and also sulphonic acids such as, for example, p-toluenesulphonic acid and 1,5-naphthalenedisulphonic acid.

Other preferred compounds according to the invention are addition products of salts of metals of main groups II to IV and of subgroups I and II as well as IV to VIII of the Periodic System of the Elements and those halogenoallyl-azolyl derivatives of the formula (I) in which $R^1$, $R^2$, $X^1$, $X^2$, $X^3$ and Y have those meanings which have been mentioned as being preferred for these substituents.

Amongst these, salts of copper, zinc, manganese, magnesium, tin, iron and of nickel are particularly preferred. Suitable anions of these salts are those which are derived from those acids which lead to physiologically acceptable addition products. Acids of this type which are particularly preferred in this connection are the hydrohalic acids such as, for example, hydrochloric acid and hydrobromic acid, furthermore phosphoric acid, nitric acid and sulphuric acid.

Examples of substances according to the invention which may be mentioned are the halogenoallyl-azolyl derivatives listed in the table below.

TABLE 1

$$X^1-C=C-CH_2-C-R^1 \quad (I)$$

with substituents $X^2$, $X^3$, $OR^2$, $CH_2$, and azolyl group containing N and Y.

| $X^1$ | $X^2$ | $X^3$ | $R^1$ | $R^2$ | Y |
|---|---|---|---|---|---|
| I | I | H | phenyl | H | N |
| F | F | H | 4-Cl-phenyl | H | N |
| I | I | H | phenyl | H | CH |
| I | I | H | 4-Cl-phenyl | H | CH |
| Cl | Cl | H | phenyl | $CH_3$ | N |
| Cl | Cl | H | phenyl | $C_2H_5$ | N |
| Cl | Cl | H | phenyl | $-CH_2-$phenyl | N |
| Cl | Cl | H | phenyl | H | N |
| Cl | Cl | H | 4-F-phenyl | H | N |

TABLE 1-continued $$X^1-\underset{X^3}{\overset{X^2}{C}}=C-CH_2-\underset{\underset{\underset{N\diagup\diagdown N}{\parallel}}{\overset{|}{CH_2}}}{\overset{OR^2}{C}}-R^1 \quad (I)$$

| $X^1$ | $X^2$ | $X^3$ | $R^1$ | $R^2$ | $Y$ |
|---|---|---|---|---|---|
| Cl | Cl | H | 2,4-difluorophenyl | H | N |
| Cl | Cl | H | 4-chlorophenyl | H | N |
| Cl | Cl | H | 3-chlorophenyl (shown as ortho in image) | H | N |
| Cl | Cl | H | 4-trifluoromethylphenyl | H | N |

If 4-(4-bromo-phenyl)-4-hydroxy-5-(1,2,4-triazol-1-yl)-pent-1-yne is used as the starting substance and a solution of chlorine gas in methylene chloride as reactant, the course of process (a) according to the invention can be illustrated by the following equation:

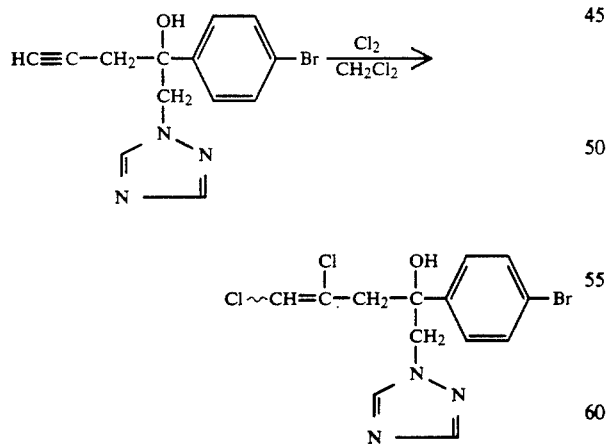

If 1,2,5-trichloro-4-hydroxy-4-[2-chloro-4-(4-chlorophenoxy)-phenyl]-pent-1-ene and 1,2,4-triazole are used as starting substances, the course of process (b) according to the invention can be illustrated by the following equation:

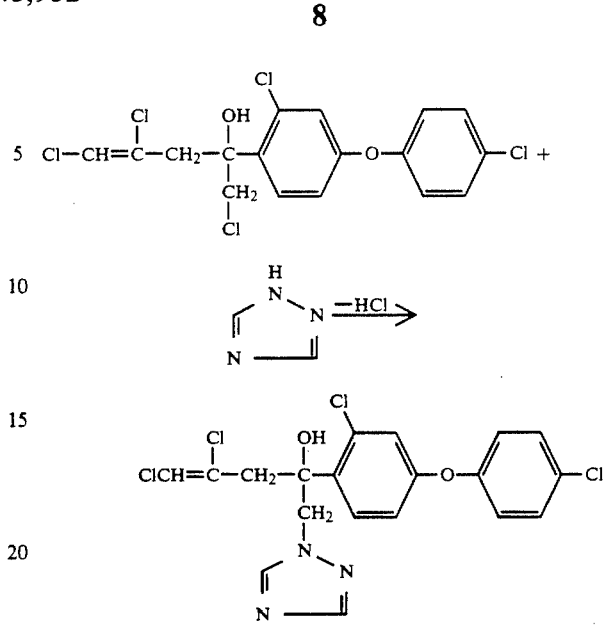

If 4-phenyl-5-(1,2,4-triazol-1-yl)-pent-1-yn-4-ol is used as starting substance and bromine in the presence of potassium hydroxide, and then bromine, as reactants, the course of process (c) according to the invention can be illustrated by the following equation:

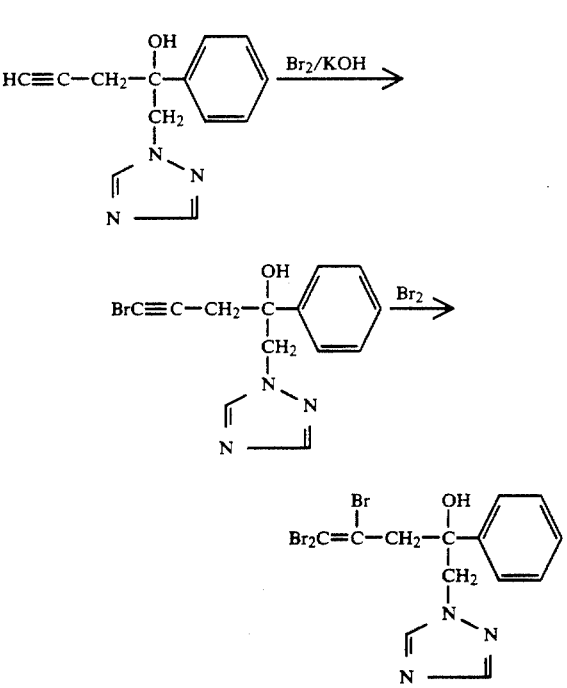

Formula (II) provides a general definition of the alkynes required as starting substances for carrying out process (a) according to the invention. In this formula, $R^1$, $R^2$ and Y preferably have those meanings which have already been mentioned in connection with the description of the substances of the formula (I) according to the invention as being preferred for these radicals.

Some of the alkynes of the formula (II) are known (compare EP-OS (European Published Specification) 0,096,786). They can be prepared by d) reacting azolyl methyl ketones of the formula

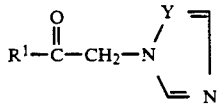 (VII)

in which
R¹ and Y have the abovementioned meanings, with propargyl halides of the formula HC≡C—CH₂—Hal    (VIII)

in which
Hal represents chlorine or bromine, in the presence of activated aluminum and in the presence of a diluent, and, if desired, reacting the resulting alkynes of the formula

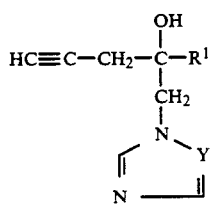 (IIa)

in which
R¹ and Y have the abovementioned meanings, with strong bases in the presence of a diluent, and reacting the resulting alcoholates of the formula

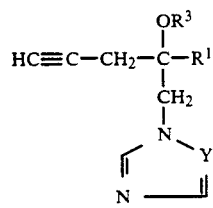 (IIb)

in which
R¹ and Y have the abovementioned meanings and
R³ represents a cationic radical of a base, with halogen compounds of the formula R⁴—Hal'    (IX)

in which
R⁴ represents alkyl, alkenyl, acyl or aralkyl and Hal' represents chlorine, bromine or iodine, in the presence of a diluent, or e) reacting chloromethyl ketones of the formula R¹—C—CH₂Cl    (X)
    ‖
    O in which
R¹ has the abovementioned meaning, with propargyl halides of the formula HC≡C—CH₂—Hal    (VIII)

in which
Hal has the abovementioned meaning, under the conditions mentioned in the first step of process (d), and then reacting the resulting hydroxyalkynes of the formula

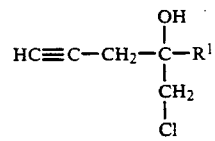 (XII)

in which
R¹ has the abovementioned meaning, with azoles of the formula

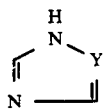 (IV)

in which
Y has the abovementioned meaning, in the presence of an acid-binding agent and in the presence of a diluent, and, if desired, further reacting the resulting alkynes of the formula

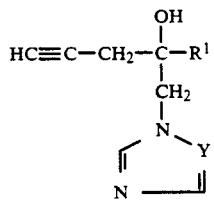 (IIa)

in which
R¹ and Y have the abovementioned meanings, in accordance with process (d).

Formula (VII) provides a general definition of the azolyl methyl ketones required as starting substances for carrying out process (d). In this formula, Y and R¹ preferably have those meanings which have already been mentioned in connection with the description of the substances of the formula (I) according to the invention as being preferred for these radicals.

The azolyl methyl ketones of the formula (VII) are known or can prepared in a simple manner by processes known in principle (compare DE-OS (German Published Specification) 2,431,407).

The propargyl halides of the formula (VIII) which are required as reactants in process (d) are known.

Diluents which can be used when carrying out the first step of process (d) are all inert organic solvents which are customary for reactions of this type. Ethers such as tetrahydrofuran or diethyl ether are preferably suitable.

The first step of process (d) is carried out in the presence of activated aluminum The latter is prepared by adding catalytic amounts of mercury(II) chloride and iodine to aluminum flakes.

When carrying out the first step of process (d), the reaction temperatures can be varied within a substantial range. In general, the process is carried out at temperatures between −80° C. and +100° C., preferably at temperatures between −70° C. and +60° C.

Process (d), as well as processes (a), (b), (c) and (e), is generally carried out under atmospheric pressure.

When carrying out the first step of process (d), the procedure is generally followed in which 1 to 2 moles of propargyl halide of the formula (VIII) and 1 to 1.5 moles of aluminum- and catalytic amounts of mercury(II) chloride and iodine are employed per mole of azolyl methyl ketone of the formula (VII). The resulting products are isolated by customary methods.

In the second step of process (d), the alkynes of the formula (IIa) are converted into the corresponding alcoholates by reacting them with suitable strong bases such as alkali metal amides or alkali metal hydrides, quaternary ammonium hydroxides or phosphonium hydroxides, in an inert diluent such as, for example, dioxane, at room temperature. Accordingly, $R^3$ in the compounds of the formula (IIb) preferably represents an alkali metal cation such as a sodium or potassium cation, or represents a quarternary ammonium or phosphonium cation.

Formula (IX) provides a general definition of the halogen compounds required as reactants for carrying out the third step of process (d). In this formula, $R^4$ preferably represents the meaning which has already been mentioned for the substituent $R^2$ in connection with the description of the substances of the formula (I) according to the invention, with the exception of the meaning of hydrogen. Hal' represents chlorine, bromine or iodine.

The halogen compounds of the formula (IX) are known or can be prepared by methods known in principle.

Suitable diluents for carrying out the second and third steps of process (d) are inert organic solvents. The following can preferably be used: ethers, such as diethyl ether or dioxane; aromatic hydrocarbons such as benzene; in individual cases also chlorinated hydrocarbons such as chloroform, methylene chloride or carbon tetrachloride; and also hexamethylphosphoric triamide.

When carrying out the second and third steps of process (d), the reaction temperatures can be varied within a substantial range. In general, the process is carried out at temperatures between 0° C. and 120° C., preferably between 20° C. and 100° C.

When carrying out the second step of process (d), alkynes of the formula (IIa) are first reacted with strong bases to give the corresponding alcoholates of the formula (IIb). In the third step which follows, preferably 1 to 2 moles of halogen compound of the formula (IX) are employed per mole of an alcoholate of the formula (IIb). To isolate the end products, the reaction mixture is freed of solvent, and the residue is treated with water and an organic solvent. The organic phase is separated off, worked up in a customary manner and purified.

In a preferred embodiment, the procedure in the second and third steps of process (d) is expediently followed in which, starting from a hydroxyl compound of the formula (IIa), the latter is converted into the alkali metal alcoholate in a suitable organic solvent by means of alkali metal hydride or alkali metal amide, and the alkali metal alcoholate is immediately reacted with a halogen compound of the formula (IX), without being isolated, in which process the compounds of the formula (II) are obtained in one pass, with the elimination of alkai metal halide.

In a further preferred embodiment, the preparation of the alcoholates and the reaction with a halogen compound of the formula (IX) are expediently carried out in a two-phase system such as, for example, aqueous sodium hydroxide or potassium hydroxide solution/toluene or methylene chloride, with the addition of 0.01-1 moles of a phase transfer catalyst such as, for example, ammonium or phosphonium compounds, during which process the alcoholates are reacted at the boundary layer or in the organic phase with the halides present in the organic phase.

Formula (X) provides a general definition of the chloromethyl ketones required as starting substances for carrying out process (e). In this formula, $R^1$ preferably has those meanings which have already been mentioned in connection with the description of the substances of the formula (I) according to the invention as being preferred for this radical.

The chloromethyl ketones of the formula (X) are known or can be prepared by methods known in principle (compare DE-OS (German Published Specification) 3,049,461).

The first step of process (e) is carried out under those conditions which are also applied to the first step of process (d).

The hydroxyalkynes of the formula (XII) can be directly further reacted with azoles of the formula (IV). Alternatively, they can first be converted into oxiranes, which can then be reacted with azoles of the formula (IV).

Suitable acid-binding agents for carrying out the second step of process (e) are all customary acid acceptors. The following can preferably be used; alkali metal carbonates and hydrogen carbonates, such as sodium carbonate, potassium carbonate or sodium hydrogen carbonate, furthermore tertiary aliphatic or aromatic amines such as triethylamine, N,N-dimethyl-cyclohexylamine, N,N-dimethyl-benzylamine and pyridine, and moreover cyclic amines such as 1,5-diazabicyclo[4.3.0]-non-5-ene (DBN), 1,8-diazabicyclo[5.4.0]undec-7-ene (DBU) and 1,4-diaza-bicyclo [2.2.2]octane (DABCO).

Suitable diluents for carrying out the second step of process (e) are all inert organic solvents. The following can preferably be used: aliphatic and aromatic, optionally halogenated hydrocarbons such as pentane, hexane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, and also tert-butyl methyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, and pyridine.

When carrying out the second step of process (e), the reaction temperatures can also be varied within a substantial range. In general, the process is carried out at temperatures between 0° C. and 200° C., preferably between 20° C. and 150° C.

When carrying out the second step of process (e), a procedure is generally followed in which an equivalent amount, or even an excess, of azole of the formula (IV) as well as 2 to 3 moles of acid-binding agent are employed per mole of hydroxyalkyne of the formula (XII). Working-up is carried out by customary methods. If a further reaction of the alkynes of the formula (IIa) is desired, the procedure in process (e) is the same as in process (d).

Suitable halogens for carrying out process (a) according to the invention are, preferably, fluorine, chlorine, bromine and iodine as reactants, furthermore mixed halogens, such as chlorine (I) fluoride, bromine (I) fluoride, iodine (I) fluoride, bromine (I) chloride, iodine (I)

chloride or iodine (I) bromide (see Methodicium Chimicum, F. Korte, Vol. 7, p. 842 (1976)).

Halogen-donating compounds which can be used are, for example, sulphuryl chloride, N-bromosuccinimide with hydrochloric acid, N-chlorosuccinimide with hydrobromic acid, or N-chlorosuccinimide with hydrogen fluoride/pyridine (see Synthesis 1973, 780).

The addition of the halogens onto the alkynes of the formula (II) can be promoted by the action of light, by heat, by radical-forming substances such as organic peroxides, by surface-active substances such as active carbon, or metal salts such as copper(II) chloride or iron(III) chloride. In some cases, this can be used for influencing the isomer ratio (E/Z) (see Houben-Weyl, Methoden der Org. Chemie [Methods in Organic Chemistry], Vol. V/3, p. 551 (1962)).

Diluents which can be employed when carrying out process (a) according to the invention are all inert organic solvents which are customary for reactions of this type. Halogenated aliphatic hydrocarbons such as methylene chloride, chloroform and carbon tetrachloride can preferably be used.

When carrying out process (a) according to the invention, the temperatures can be varied within a certain range. In general, the process is carried out at temperatures between $-10°$ C. and $+120°$ C., preferably between $-5°$ C. and $+80°$ C.

When carrying out process (a) according to the invention, an equivalent amount or an excess of halogen, or halogen-donating compound, is generally employed per mole of alkyne of the formula (II). Working-up is carried out by customary methods. In general, a procedure is followed in which the mixture is diluted using an organic solvent which is sparingly soluble in water, the diluted mixture is washed with water, and the organic phase is first dried and then concentrated. However, when the reaction is complete, it is also possible to concentrate the reaction mixture directly by stripping off the volatile components under reduced pressure. If desired, the resulting products can be further purified by customary methods.

Formula (III) provides a general definition of the alkenes required as starting substances in process (b) according to the invention. In this formula, $R^1$, $R^2$, $X^1$ and $X^2$ preferably have those meanings which have already been mentioned in connection with the description of the substances of the formula (I) according to the invention as being preferred for these substances. Z preferably represents chlorine, bromine, iodine, methylsulphonate or p-tolylsulphonate.

The alkenes of the formula (III) can be prepared by customary methods. For example, alkenes of the formula (III) are obtained by reacting hydroxyalkines of the formula (XII) with halogens in the presence of a diluent. In this reaction, the reaction conditions correspond to those applied in the case of process (a) according to the invention.

Suitable diluents for carrying out process (b) according to the invention are all customary inert organic solvents. Those solvents which have already been mentioned in connection with the description of the second step of process (e) as being preferred solvents can preferably be used.

Suitable acid-binding agents for carrying out process (b) according to the invention are all customary acid acceptors. All those acid-binding agents which have already been mentioned in connection with the description of the second step of process (e) as being preferred acid acceptors can preferably be used.

When carrying out process (b) according to the invention, the reaction temperatures can be varied within a substantial range. In general, the process is carried out at temperatures between $0°$ C. and $150°$ C., preferably between $20°$ C. and $120°$ C.

When carrying out process (b) according to the invention, a procedure is generally followed in which an equivalent amount or an excess of azole of the formula (IV) as well as 2 to 3 moles of acid-binding agent are employed per mole of alkene of the formula (III). Working-up is carried out by customary methods.

Formula (V) provides a general definition of the hypohalites required as reactants for carrying out process (c) according to the invention. In this formula, M preferably represents a sodium or potassium ion, and $X^4$ preferably represents chlorine, bromine or iodine. The hypohalite is preferably prepared freshly from base and halogen.

Diluents which can be employed for carrying out process (c) according to the invention, when carrying out the first as well as the second step, are all inert organic solvents which are customary for reactions of this type. The following can preferably be used: halogenated aliphatic hydrocarbons such as methylene chloride, chloroform and carbon tetrachloride.

When carrying out process (c) according to the invention, the temperatures can be varied within a certain range, in the first as well as in the second step. In general, the process is carried out at temperatures between $-10°$ C. and $+120°$ C., preferably between $-5°$ C. and $+80°$ C.

When carrying out the first step of process-(c) according to the invention, an excess of hypohalite is generally employed per mole of alkyne of the formula (II). When carrying out the second step of process (c) according to the invention, an equivalent amount or an excess of halogen is generally employed per mole of halogenoalkyne of the formula (VI). When carrying out the first as well as the second step, working-up is carried out by customary methods.

The halogenoallyl-azolyl derivatives of the formula (I) which can be obtained by the processes according to the invention can be converted into acid addition salts or metal salt complexes.

To prepare acid addition salts of compounds of the formula (I), those acids are preferably suitable which have already been mentioned in connection with the description of the acid addition salts according to the invention as being preferred acids.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and, if desired, purified by washing with an inert organic solvent.

To prepare metal salt complexes of the compounds of the formula (I), those salts of metals are preferably suitable which have already been mentioned in connection with the description of the metal salt complexes according to the invention as being preferred.

The metal salt complexes of the compounds of the formula (I) can obtained in a simple manner by customary methods, for example by dissolving the metal salt in alcohol, for example ethanol, and adding the solution to compounds of the formula (I). Metal salt complexes can be isolated in a known manner, for example by filtration, and, if desired, purified by recrystallization.

The active compounds according to the invention have a powerful microbicidal action and can be employed as fungicides for combating undesired microorganisms, such as fungi and bacteria, in plant protection and in the protection of materials.

Fungicides are employed in plant protection for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as Xanthomonas oryzae; Pseudomonas species, such as Pseudomonas lachrymans; Erwinia species, such as Erwinia amylovora; Pythium species, such as Pythium ultimum; Phytophthora species, such as Phytophthora infestans; Pseudoperonospora species, such as Pseudoperonospora humuli or Pseudoperonospora cubensis; Plasmopara species, such as Plasmopara viticola; Peronospora species, such as Peronospora pisi or P. brassicae; Erysiphe species, such as Erysiphe graminis; Sphaerotheca species, such as Sphaerotheca fuliginea; Podosphaera species, such as Podosphaera leucotricha; Venturia species, such as Venturia inaequalis; Pyrenophora species, such as Pyrenophora teres or P. graminea (conidia form: Drechslera, syn: Helminthosporium); Cochliobolus species, such as Cochliobolus sativus (conidia form: Drechslera, syn: Helminthosporium); Uromyces species, such as Uromyces appendiculatus; Puccinia species, such as Puccinia recondita; Tilletia species, such as Tilletia caries; Ustilago species, such as Ustilago nuda or Ustilago avenae; Pellicularia species, such as Pellicularia sasakii; Pyricularia species, such as Pyricularia oryzae; Fusarium species, such as Fusarium culmorum; Botrytis species, such as Botrytis cinerea; Septoria species, such as Septoria nodorum; Leptosphaeria species, such as Leptosphaeria nodorum; Cercospora species, such as Cercospora canescens; Alternaria species, such as Alternaria brassicae and Pseudocercosporella species, such as Pseudocercosporella herpotrichoides.

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating cereal and rice diseases, such as Pseudocercosporella, Erysiphe, Fusarium, Pyrenophora, Cochliobolus, Pyricularia and Pellicularia, as well as for combating mildew on cucumbers and apple scab, and furthermore for combating Botrytis in fruit growing, viticulture and vegetable growing. Moreover, they have a good and broad in vitro action and are also suitable for combating -powdery mildews such as Rhizoctonia solani.

In the protection of materials, the substances according to the invention can be employed for the protection of industrial materials against attack and destruction by undesired microorganisms.

Industrial materials in the present connection are understood as meaning non-living materials which have been prepared for use in industry. For example, industrial materials which are to protected from microbial change or destruction by active compounds according to the invention, are glues, sizes, paper and board, textiles, leather, wood, paints and plastic articles, cooling lubricants and other materials which can be attacked or destroyed by microorganisms. Within the scope of the materials to be protected, parts of production plants which can be impaired by the multiplication of microorganisms may also be mentioned, for example cooling water circuits. Industrial materials which may preferably be mentioned within the scope of the present invention are glues, sizes, papers and boards, leather, wood, paints, cooling lubricants and heat-transfer liquids, particularly preferably wood.

Examples of microorganisms which may mentioned, which can cause degradation or change in the industrial materials, are bacteria, fungi, yeasts, algae and slime organisms. The active compounds according to the invention preferably act against fungi, in particular mold, fungi which discolor and destroy wood (Basidiomycetes), and also against slime organisms and algae.

Microorganisms of the following genera may be mentioned by way of example: Alternaria, such as Alternaria tenuis, Aspergillus, such as Aspergillus niger, Chaetomium, such as Chaetomium globosum, Coniophora, such as Coniophora puetana, Lentinus, such as Lentinus tigrinus, Penicillium, such as Penicillium glaucum, Polyporus, such as Polyporus versicolor, Aureobasidium, such as Aureobasidium pullulans, Sclerophoma, such as Sclerophoma pityophila, Trichoderma, such as Trichoderma viride, Escherichia, such as Escherichia coli, Pseudomonas, such as Pseudomonas aeruginosa, Staphylococcus, such as Staphylococcus aureus.

Depending on their particular physical and/or chemical properties, the active compounds can be converted into the customary formulations, such as solutions, emulsions, suspensions, powders, foams, pastes, granules, aerosols, very fine capsules in polymeric substances and in coating compositions for seed, ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogeno hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable:

for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron manganese, boron, copper, cobalt, molybdenum and zinc.

The formulations in plant protection generally contain between 0.1 and 95 per cent by weight of active compound, preferably between 0.5 and 90%.

When used in plant protection, the active compounds according to the invention can be present in the formulations as a mixture with other known active compounds such as fungicides, insecticides, acaricides and herbicides, as well as in mixtures with fertilizers and growth regulators. When used in plant protection, the active compounds can be used as such, in the form of their formulations or the use forms prepared from these, such as ready-for-use solutions, suspensions, wettable powders, pastes, soluble powders, dusting agents and granules. They are applied in the customary manner, for example by watering, spraying, atomizing, scattering, dusting, foaming, brushing on and the like. It is furthermore possible to apply the active compounds by the ultra-low-volume method, or to inject the preparation of active compound, or the active compound itself, into the soil. The seed of plants can also be treated.

In the treatment of parts of plants, the active compound concentrations in the use forms can be varied within a substantial range. In general, they are between 1 and 0.0001% by weight, preferably between 0.5 and 0.001%.

In the treatment of seeds, amounts of active compound of 0.001 to 50 g per kg of seed, preferably 0.01 to 10 g, are generally required.

In the treatment of the soil, active compound concentrations of 0.00001 to 0.1% by weight, preferably of 0.0001 to 0.02%, are required at the site of action.

The microbicidal agents used for the protection of industrial materials generally contain the active compounds in an amount of 1 to 95% by weight, preferably of 10 to 75% by weight.

When used in the protection of materials, the use concentrations of active compounds according to the invention depend on the nature and the occurrence of the microorganisms to be combated as well as on the composition of the material to be protected. The optimum application rate can be determined by a series of tests. In general, the application concentrations are in a range of from 0.001 to 5% by weight, preferably from 0.05 to 1.0% by weight, based on the material to be protected.

When used in the protection of materials, the active compounds according to the invention can also be applied as a mixture with other known active compounds.

The following active compounds may be mentioned by way of example: benzyl alcohol mono(poly)hemiformal and other formaldehyde-releasing compounds, benzimidazolyl methylcarbamate, tetramethylthiuram disulphide, zinc salts of dialkyl dithiocarbamates, 2,4,5,6-tetrachloroisophthalonitrile, thiazolylbenzimidazole, mercaptobenzothiazole, 2-thiocyanatomethylthiobenzothiazole, methylene bisthiocyanate, phenol derivatives such as 2-phenylphenol, (2,2'-dihydroxy-5,5'-dichloro)-diphenylmethane and 3-methyl-4-chlorophenol, organotin compounds, N-trihalogenomethylthio compounds such as folpet, fluorofolpet and dichlofluanide.

The preparation and the use of the active compounds according to the invention are illustrated by the examples which follow.

PREPARATION EXAMPLES

EXAMPLE 1

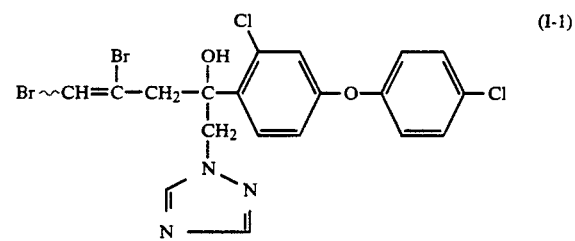

0.8 g (8 mmol) of concentrated sulphuric acid is slowly added dropwise at 0° C. with stirring to a solution of 3 g (7.7 mmol) of 4-[2-chloro-4-(4-chlorophenoxy)-phenyl]-5-(1,2,4-triazol-1-yl)-pent-1-yn-4-ol in 15 ml of dichloromethane. A solution of 1.4 g (8.75 mmol) of bromine in 10 ml of dichloromethane is then added dropwise with exposure to light and with stirring. The temperature of the reaction mixture is allowed to rise to room temperature and the mixture is stirred for a further hour at room temperature. The reaction mixture is extracted by shaking twice in each case with aqueous sodium carbonate solution and with water, and the organic phase is then dried over sodium sulphate and concentrated by stripping off the volatile components under reduced pressure. In this manner, 4.1 g (100% of theory) of 4-(2-chloro-4-(4-chlorophenoxy)-phenyl)-1,2-dibromo-5-(1,2,4-triazol-1-yl)-pent-1-en-4-ol are obtained in the form of an oil.

$^1$H-NMR (200 MHz, CDCl$_3$):

δ=3.42 (d, 1H), 3.58 (d, 1H), 4.6 (broad, 1H), 4.76 (d, 1H), 5.42 (d, 1H), 6.68 (s, 1H), 6.78 (dd, 1H), 6.86–7.0 (m, 3H), 7.33 (d, 2H), 7.65 (d, 1H), 7.87 (s, 1H), 8.20 (s, 1H) ppm Preparation of the starting substance:

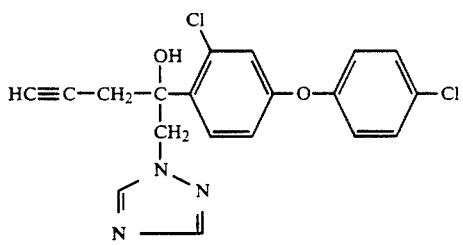

(II-1)

1.05 g (39 mmol) of aluminum flakes, a spatula tipful of mercury chloride and an iodine crystal are warmed at 40° C. for one hour in 5 ml of absolute tetrahydrofuran under a nitrogen atmosphere. The mixture is heated to 60° C. and 6.9 g (58 mmol) of propargyl bromide in 10 ml of absolute tetrahydrofuran are added dropwise. The mixture is subsequently stirred at 60° C. for 60 minutes and then cooled to −60° C. A solution of 10 g (29 mmol) of 1-[2-chloro-4-(4-chloro-phenoxy)-phenyl]-2-(1,2,4-triazol-1-yl)-ethan-1-one in 20 ml of absolute tetrahydrofuran is then added dropwise and the mixture is subsequently allowed to react first for 1 hour at 0° C. and then for 2 hours at room temperature. 20 ml of a saturated aqueous ammonium chloride solution are added, the precipitate obtained is filtered off with suction, and the filtrate is concentrated under reduced pressure. The residue is taken up in ethyl acetate, and the resulting solution is washed with water, dried over sodium sulphate and concentrated under reduced pressure. In this manner, 8.8 g (80% of theory) of 4-(2-chloro-4-(4-chlorophenoxy)-phenyl)-5-(1,2,4-triazol-1-yl)-pent-1-yn-4-ol are obtained in the form of a solid of melting point 124° C.

The substances of the formula

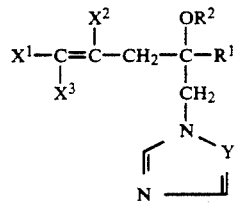

(I)

shown in Table 2 below are also prepared by the methods indicated above.

TABLE 2

| Example No. | Compound No. | $X^1$ | $X^2$ | $X^3$ | $R^1$ | $R^2$ | Y | Melting point (°C.) or $^1$H-NMR (CDCl$_3$, 200 MHz) |
|---|---|---|---|---|---|---|---|---|
| 2 | I-2 | Br | Br | H | phenyl | H | N | δ = 3.12(d, 1H), 3.32(d, 1H), 4.62(s, 2H), 6.58(s, 1H), 7.23–7.36(m, 3H), 7.4–7.48 (m, 3H), 7.8(s, 1H), 7.9(s, 1H)ppm |
| 3 | I-3 | Br | Br | H | 4-Cl-phenyl | H | N | δ = 3.18(d, 1H), 3.29(d, 1H), 4.61(s, 2H), 6.60(s, 1H), 7.29(d, 2H), 7.37(d, 2H), 7.86(s, 1H), 8.04(s, 1H)ppm |
| 4 | I-4 | Br | Br | H | 4-Br-phenyl | H | N | δ = 3.18(d, 1H), 3.28(d, 1H), 4.60(s, 2H), 5.32(s, 1H), 6.61(s, 1H), 7.28(d, 2H), 7.45(d, 2H), 7.87(s, 1H), 7.98(s, 1H)ppm |
| 5 | I-5 | Br | Br | H | 2,4-F$_2$-phenyl | H | N | 146° C. |
| 6 | I-6 | Br | Br | H | 2,4-Cl$_2$-phenyl | H | N | δ = 2.95–3.29(m, 2H), 4.52 and 4.57(each s, ε2H), 6.62 and 6.74(each s, ε1H), 7.23–7.28 (m, 2H), 7.35(d, 1H), 7.86–8.05(m, 2H)ppm isomers |
| 7 | I-7 | Br | Br | H | biphenyl | H | N | 117° C. |
| 8 | I-8 | Cl | Cl | H | 4-Br-phenyl | H | N | δ = 3.15(AB, 2H), 4.6–4.7(AB, 2H)6.6(s, 1H), 7.25 and 7.45 (2d, 4H), 7.95(s, 1H), 8.15 (s, 1H) |

TABLE 2-continued

| Example No. | Compound No. | $X^1$ | $X^2$ | $X^3$ | $R^1$ | $R^2$ | Y | Melting point (°C.) or $^1$H-NMR (CDCl$_3$, 200 MHz) |
|---|---|---|---|---|---|---|---|---|
| 9 | I-9 | Cl | Cl | H | 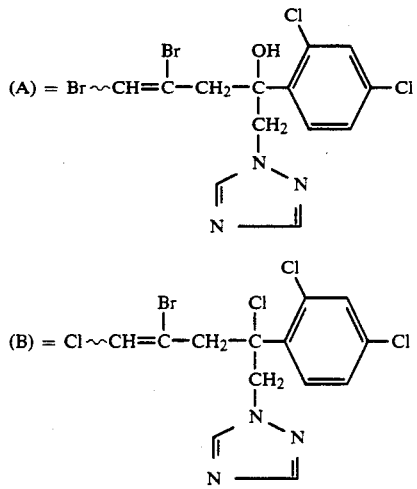 | H | N | 50–55° (isomer mixture) |

The compounds of the formulae indicated below were employed as comparison substances in the following Use Examples:

(A) = Br∼CH=C(Br)—CH$_2$—C(OH)(2,4-Cl$_2$C$_6$H$_3$)—CH$_2$-(1,2,4-triazol-1-yl)

(B) = Cl∼CH=C(Br)—CH$_2$—C(Cl)(2,4-Cl$_2$C$_6$H$_3$)—CH$_2$-(1,2,4-triazol-1-yl)

(Disclosed in EP-OS 0,097,425).

EXAMPLE A

| Erysiphe test (barley)/protective | |
|---|---|
| Solvent: | 100 parts by weight of dimethylformamide |
| Emulsifier: | 0.25 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compounds (I-2), (I-5), (I-6) and (I-8) according to the invention show a very good action.

EXAMPLE B

| Erysiphe test (wheat)/protective | |
|---|---|
| Solvent: | 100 parts by weight of dimethylformamide |
| Emulsifier: | 0.25 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compounds (I-1), (I-5), (I-6) and (I-8) according to the invention show a better activity than the comparison substances (A) and (B).

EXAMPLE C

| Pyrenophora teres test (barley)/protective | |
|---|---|
| Solvent: | 100 parts by weight of dimethylformamide |
| Emulsifier: | 0.25 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Pyrenophora teres. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, compound (I-9) according to the invention shows a very good activity.

EXAMPLE D

Erysiphe test (barley)/seed treatment

The active compounds are used as dry dressings. They are prepared by extending the respective active compound with ground mineral to give a finely powdered mixture which ensures a uniform distribution on the surface of the seed.

For dressing, the seed is shaken for 3 minutes with the dressing in a closed glass container.

The barley is sown using 3×12 grains 2 cm deep in standard soil. 7 days after sowing, when the young plants have unfolded their first leaf, they are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compounds (I-2), (I-8) and (I-9) according to the invention show a better activity than the comparison substance (B).

EXAMPLE E

| Pyricularia test (rice)/protective | |
|---|---|
| Solvent: | 12.5 parts by weight of acetone |
| Emulsifier: | 0.3 parts by weight of alkylaryl polyglycol ether |

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, compound (I-8) according to the invention shows a better activity than the comparison substance (A).

EXAMPLE F

| Pellicularia test (rice) | |
|---|---|
| Solvent: | 12.5 parts by weight of acetone |
| Emulsifier: | 0.3 parts by weight of alkylaryl polyglycol ether |

To produce a suitable preparation of active compound, 1 part by weight of active compound is mixed with the stated amount of solvent, and the concentrate is diluted with water and the stated amount of emulsifier to the desired concentration.

To test for activity, young rice plants in the 3 to 4 leaf stage are sprayed until dripping wet. The plants remain in a greenhouse until they have dried off. The plants are then inoculated with Pellicularia sasakii and are placed at 25° C. and 100% relative atmospheric humidity.

The evaluation of the disease infestation is carried out 5 to 8 days after the inoculation.

In this test, compound (I-8) according to the invention shows a better activity than the comparison substance (B).

EXAMPLE G

| Botrytis test (bean)/protective | |
|---|---|
| Solvent: | 4.7 parts by weight of acetone |
| Emulsifier: | 0.3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, compound (I-5) according to the invention shows a very good activity.

EXAMPLE H

| Venturia test (apple)/protective systemic | |
|---|---|
| Solvent: | 4.7 parts by weight of acetone |
| Emulsifier: | 0.3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, compounds (I-2), (I-4), (I-5), (I-6) and (I-8) according to the invention show a very good activity.

It will be understood that the specification and examples are illustrative but not limitative of the present invention and that other embodiments within the spirit and scope of the invention will sugget themselves to those skilled in the art.

We claim:

1. A halogenoallyl-azolyl derivative of the formula $$X^1-C(X^3)=C(X^2)-CH_2-C(OH)(R^1)-CH_2-N\langle\begin{array}{c}N\\N\end{array}\rangle$$

in which

R¹ represents a radical of the formula

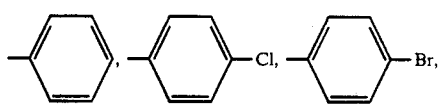

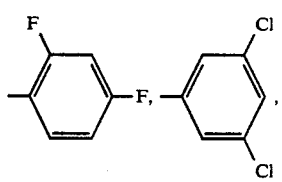

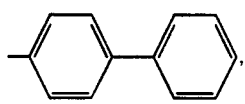

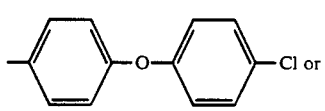

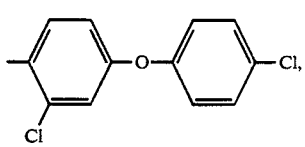

X¹ represents chlorine or bromine,

X² represents chlorine or bromine, and

X³ represents hydrogen, chlorine or bromine, or an addition product thereof with an acid or metal salt.

2. A compound according to claim 1, wherein such compound is 4-(2-chloro-4-(4-chlorophenoxy)-phenyl)-1,2-dibromo-5-(1,2,4-triazol-1-yl)-pent-1-en-4-ol of the formula

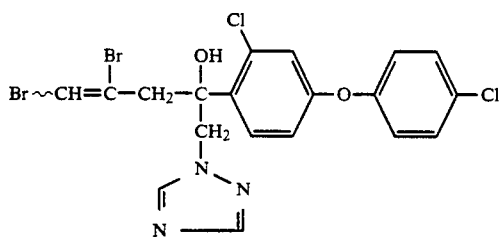

or an addition product thereof with an acid or metal salt.

3. A compound according to claim 1, wherein such compound is 4-phenyl-1,2-dibromo-5-(1,2,4-triazol-1-yl)-pent-1-en-4-ol of the formula

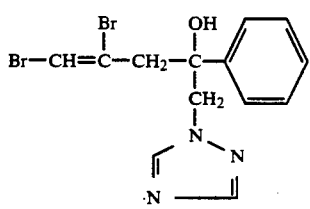

or an addition product thereof with an acid or metal salt.

4. A compound according to claim 1, wherein such compound is 4-(4-bromophenyl)-1,2-dibromo-5-(1,2,4-triazol-1-yl)-pent-1-en-4-ol of the formula

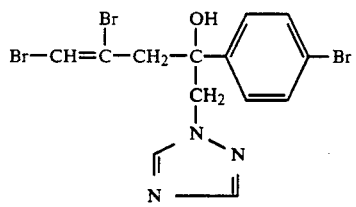

or an addition product thereof with an acid or metal salt.

5. A compound according to claim 1, wherein such -pent-1-en-4-ol of the formula

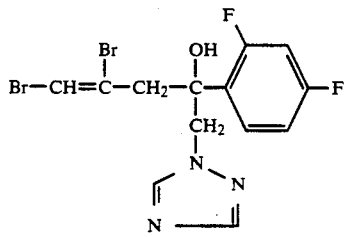

or an addition product thereof with an acid or metal salt.

6. A compound according to claim 1, wherein such compound is 4-(3,5-dichlorophenyl)-1,2-dichloro-5-(1,2,4-triazol-1-yl)-pent-1-en-4-ol of the formula

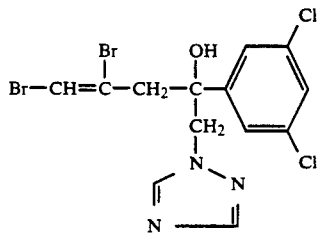

or an addition product thereof with an acid or metal salt.

7. A microbicidal composition comprising a microbicidally effective amount of a compound or addition product thereof according to claim 1 and an inert diluent.

8. A method of combating microbes which comprises applying to such microbes or to a habitat from which it is desired to exclude such microbes a microbicidally effective amount of a compound or addition product thereof according to claim 1.

9. The method according to claim 8, wherein such compound is 4-(2-chloro-4-(4-chlorophenoxy)-phenyl)-1,2-dibromo-5-(1,2,4-triazol-1-yl)-pent-1-en-4-ol, 4-phenyl-1,2-dibromo-5-(1,2,4-triazol-1-yl)-pent-1-en-4-ol, 4-(4-bromophenyl)-1,2-dibromo-5-(1,2,4-triazol-1-yl)-pent-1-en-4-ol, 4-(2,4-difluorophenyl)-1,2-dibromo-5-(1,2,4-triazol-1-yl)-pent-1-en-4-ol or 4-(3,5-dichlorophenyl)-1,2-dichloro-5-(1,2,4-triazol-1-yl)-pent-1-en-4-ol, or an addition product thereof with an acid or metal salt.

* * * * *

UNITED STATES PATENT AND TRADEMARK OFFICE
CERTIFICATE OF CORRECTION

PATENT NO. : 5,143,932
DATED : September 1, 1992
INVENTOR(S) : Jautelat et al.

It is certified that error appears in the above-identified patent and that said Letters Patent is hereby corrected as shown below:

Col. 26, lines 16-17    After " such " insert -- compound is 4-(2,4-difluorophenyl)-1,2-dibromo-5-(1,2,4-triazol-1-yl) --

Signed and Sealed this

First Day of March, 1994

Attest:

BRUCE LEHMAN

Attesting Officer    Commissioner of Patents and Trademarks